(12) United States Patent
Kozloski et al.

(10) Patent No.: US 11,682,476 B2
(45) Date of Patent: Jun. 20, 2023

(54) UPDATING A PRESCRIPTION STATUS BASED ON A MEASURE OF TRUST DYNAMICS

(71) Applicant: International Business Machines Corporation, Armonk, NY (US)

(72) Inventors: James R. Kozloski, New Fairfield, CT (US); Sara Berger, White Plains, NY (US); Anup Kalia, Elmsford, NY (US); Jeffrey L. Rogers, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 153 days.

(21) Appl. No.: 17/134,954

(22) Filed: Dec. 28, 2020

(65) Prior Publication Data

US 2021/0118541 A1 Apr. 22, 2021

Related U.S. Application Data

(63) Continuation of application No. 15/986,598, filed on May 22, 2018, now Pat. No. 10,957,434.

(51) Int. Cl.
*G16H 20/10* (2018.01)
*G06N 20/00* (2019.01)

(52) U.S. Cl.
CPC ............. *G16H 20/10* (2018.01); *G06N 20/00* (2019.01)

(58) Field of Classification Search
CPC ............................... G16H 20/10; G06N 20/00
USPC ........................................................ 705/2–3
See application file for complete search history.

(56) References Cited

U.S. PATENT DOCUMENTS

| 5,908,383 | A | 6/1999 | Brynjestad |
| 6,249,809 | B1 | 6/2001 | Bro |
| 7,229,430 | B2 | 6/2007 | Hickle et al. |
| 7,251,609 | B1 * | 7/2007 | McAlindon ............ G16H 70/40 707/999.009 |

(Continued)

FOREIGN PATENT DOCUMENTS

| CN | 102314558 A | 1/2012 |
| CN | 105844112 A | 8/2016 |

OTHER PUBLICATIONS

Notice of Allowance received for U.S. Appl. No. 15/986,409 dated Jan. 7, 2021, 44 pages.

(Continued)

*Primary Examiner* — Michael Tomaszewski
(74) *Attorney, Agent, or Firm* — Amin, Turocy & Watson, LLP

(57) ABSTRACT

Techniques regarding autonomously updating the status of a prescription are provided. For example, one or more embodiments described herein can comprise a system, which can comprise a memory that can store computer executable components. The system can also comprise a processor, operably coupled to the memory, and that can execute the computer executable components stored in the memory. The computer executable components can comprise a prescription component that can update a status of a prescription associated with an entity based on a trust disposition value. The trust disposition value can be determined using machine learning technology and can be indicative of an expected effectiveness of the prescription.

20 Claims, 10 Drawing Sheets

(56) References Cited

U.S. PATENT DOCUMENTS

| | | | |
|---|---|---|---|
| 7,463,927 | B1 | 12/2008 | Chaouat |
| 7,957,809 | B2 | 6/2011 | Bourget et al. |
| 8,046,241 | B1 | 10/2011 | Dodson |
| 8,086,563 | B2 | 12/2011 | Jung et al. |
| 8,380,314 | B2 | 2/2013 | Panken et al. |
| 8,380,531 | B2 | 2/2013 | Paty et al. |
| 8,469,713 | B2 | 6/2013 | Kron et al. |
| 8,636,273 | B2 | 1/2014 | Saito |
| 9,147,041 | B2 | 9/2015 | Amarasingham et al. |
| 9,262,688 | B1 | 2/2016 | Zadeh |
| 9,536,049 | B2 | 1/2017 | Brown et al. |
| 9,782,122 | B1 | 10/2017 | Pulliam et al. |
| 2001/0012913 | A1 | 8/2001 | Iliff |
| 2002/0128866 | A1 | 9/2002 | Goetzke et al. |
| 2003/0178031 | A1 | 9/2003 | Du Pen et al. |
| 2004/0064709 | A1 | 4/2004 | Heath |
| 2006/0293572 | A1 | 12/2006 | Bulat |
| 2007/0271272 | A1 | 11/2007 | McGuire et al. |
| 2008/0059241 | A1* | 3/2008 | Zahlmann ............... G16H 10/20 705/3 |
| 2009/0157141 | A1 | 6/2009 | Chiao et al. |
| 2010/0087795 | A1 | 4/2010 | Krijnsen et al. |
| 2010/0153832 | A1 | 6/2010 | Markus et al. |
| 2011/0035158 | A1 | 2/2011 | Banos et al. |
| 2011/0054564 | A1 | 3/2011 | Valencia |
| 2012/0078837 | A1 | 3/2012 | Bagchi et al. |
| 2012/0316898 | A1* | 12/2012 | Levitt .................... G16H 10/20 705/3 |
| 2013/0173277 | A1 | 7/2013 | Eller et al. |
| 2013/0244336 | A1 | 9/2013 | Mayer et al. |
| 2014/0074454 | A1 | 3/2014 | Brown et al. |
| 2014/0074509 | A1 | 3/2014 | Amarasingham et al. |
| 2014/0275827 | A1 | 9/2014 | Gill et al. |
| 2014/0276188 | A1 | 9/2014 | Jardin |
| 2014/0316793 | A1* | 10/2014 | Pruit ...................... G16H 10/20 705/2 |
| 2015/0019241 | A1 | 1/2015 | Bennett et al. |
| 2015/0193583 | A1 | 7/2015 | McNair et al. |
| 2015/0199484 | A1 | 7/2015 | Morris et al. |
| 2015/0254408 | A1 | 9/2015 | Dadlani Mahtani et al. |
| 2015/0278474 | A1* | 10/2015 | Stueckemann ........ G06Q 10/10 705/2 |
| 2015/0287330 | A1 | 10/2015 | Kron et al. |
| 2016/0100790 | A1 | 4/2016 | Cantu et al. |
| 2016/0117484 | A1 | 4/2016 | Hanina et al. |
| 2016/0198996 | A1 | 7/2016 | Dullen |
| 2016/0210424 | A1 | 7/2016 | Di Battista |
| 2016/0213314 | A1 | 7/2016 | Zuckerman-Stark et al. |
| 2016/0335412 | A1 | 11/2016 | Tucker et al. |
| 2016/0339241 | A1 | 11/2016 | Hargrove et al. |
| 2017/0004260 | A1 | 1/2017 | Moturu et al. |
| 2017/0056642 | A1 | 3/2017 | Moffitt et al. |
| 2017/0124269 | A1 | 5/2017 | McNair et al. |
| 2018/0018966 | A1 | 1/2018 | Leonard |
| 2018/0039763 | A1* | 2/2018 | Tidor .................... G16H 10/20 |
| 2018/0278554 | A1 | 9/2018 | Kassabgi |
| 2018/0307678 | A1 | 10/2018 | Anantaram et al. |
| 2019/0140986 | A1 | 5/2019 | Anderson et al. |

OTHER PUBLICATIONS

Non-Final Office Action received for U.S. Appl. No. 15/986,564 dated May 4, 2021, 61 pages.

Final Office Action received for U.S. Appl. No. 15/986,409 dated Oct. 2, 2020, 44 pages.

Baker, et al., Experience and knowledge of pain management in patients receiving outpatient cancer treatment: What do older adults really know about their cancer pain?, Pain Medicine, 2014, pp. 52-60, vol. 15. No. 1.

Hallenbeck, Pain and Intercultural Communication, Handbook of Pain and Palliative Care, Chapter 2, 2013, 24 Pages.

Pinto, et al., Patient-centred communication is associated with positive therapeutic alliance: a systematic review, Journal of Physiotherapy, 2012, pp. 77-87. vol. 58.

Anonymous, Method and System for Enhanced Medication Management System, Nov. 25, 2016, 5 Pages.

Kalia, et al., Goven: estimating trust from communications, Journal of Trust Management, 2016, 19 Pages, vol. 3, No. 1.

Anonymous, Methods & devices for managing and monitoring arthritis patients, IP.com No. IPCOM000247325D; Aug. 23, 2016, 7 pages.

Temple, Enrichment Strategies for Clinical Trials, CDER Enrichment Webinar, Mar. 25, 2013, 40 Pages.

Victor, et al., Trustworthiness as a Clinical Variable: The Problem of Trust in the Management of Chronic, Nonmalignant Pain, Pain Medicine, 2005, pp. 385-391, vol. 6, No. 5.

Buchman, et al., You Present like a Drug Addict: Patient and Clinician Perspectives on Trust and Trustworthiness in Chronic Pain Management, Pain Medicine, 2016, pp. 1394-1406, vol. 17.

Castle, et al., Neural and behavioral bases of age differences in perceptions of trust, PNAS, Dec. 12, 2012, pp. 20848-20852, vol. 109, No. 51.

Baliki, et al, Brain Morphological Signatures for Chronic Pain, PLoS ONE, Oct. 13, 2011, 13 Pages, vol. 6, No. 10.

Eickhoff, et al., Functional Segregation of the Human Dorsomedial Prefrontal Cortex, Cerebral Cortex, Jan. 2016, pp. 304-321, vol. 26.

Hashmi, et al., Shape shifting pain: chronification of back pain shifts brain representation from nociceptive to emotional circuits, Brain A Journal of Neurology, Jun. 14, 2013, pp. 2751-2768, vol. 136.

Fett, et al., Social neuroscience in psychiatry: unravelling the neural mechanisms of social dysfunction, Psychological Medicine, Sep. 18, 2014, 21 Pages.

Tsukiura, et al., Insular and hippocampal contributions to remembering people with an impression of bad personality, SCAN, 2013, pp. 515-522, vol. 8.

Vachon-Presseau, et al., Corticolimbic anatomical characteristics predetermine risk for chronic pain, Brain A Journal of Neurology, 2016, pp. 1958-1970, vol. 139.

Getov, et al., Human brain structure predicts individual differences in preconscious evaluation of facial dominance and trustworthiness, SCAN, 2015, pp. 690-699, vol. 10.

Mansour, et al., Brain white matter structural properties predict transition to chronic pain, Pain, Oct. 2013, pp. 2160-2168, vol. 154, No. 10.

Baliki, et al., Corticostrialal functional connectivity predicts transition to chronic back pain, National Neuroscience, pp. 1117-1119, vol. 15, No. 8.

Sprengelmeyer, et al., The neuropsychology of first impressions: Evidence from Huntington's disease, Cortex, Dec. 10, 2016, 41 Pages.

Baliki, et al., Predicting value of pain and analgesia: nucleus accumbens response to noxious stimuli changes in the presence of chronic pain, Neuron, Apr. 15, 2010, pp. 149-160, vol. 66, No. 1.

Tetreault, et al., Brain Connectivity Predicts Placebo Response across Chronic Pain Clinical Trials, PLOS Biology, Oct. 27, 2016, vol. 14, No. 10.

Pecina, et al., Personality Trait Predictors of Placebo Analgesia and Neurobiological Correlates, Neuropsychopharmacology, 2013, pp. 639-646, vol. 38.

Schaler, et al., Health Care Providers' Judgments in Chronic Pan: The Influence of Gender and Trustworthiness, International Association for the Study of Pain, 2016, 32 Pages.

Colloca, et al., Placebo analgesia induced by social observational learning, Pain, Jan. 29, 2009, pp. 28-34, vol. 144.

Geers, et al., Reconsidering the role of personality in placebo effects: Dispositional optimism, situational expectations, and the placebo response, Journal of Psychosomatic Research, 2005, pp. 121-127, vol. 58.

Hyland, et al., Motivational concordance: An important mechanism in self-help therapeutic rituals involving inert (placebo) substances, Journal of Psychosomatic Research, 2008, pp. 405-413, vol. 65.

Tuttle, et al., Increasing placebo responses over lime in U.S. clinical trials of neuropalhic pain, Pain, Dec. 2015, pp. 2616-2626, vol. 156.

(56) References Cited

OTHER PUBLICATIONS

Lount, The Impact of Positive Mood on Trust in Interpersonal and Intergroup Interactions, Journal of Personality and Social Psychology, 2010, pp. 420-433, vol. 98, No. 3.

Sessa, et al., Perceived trustworthiness shapes neural empathic responses toward others' pain, Neuropsychologia, 2015, pp. 97-105, vol. 79.

Mel, et al., The NIST Definition of Cloud Computing, National Institute of Standards and Technology Special Publication 800-145, Sep. 2011, 7 Pages.

Mutso et al., "Reorganization of hippocampal functional connectivity with transition to chronic back pain," Journal of Neurophysiology, 2014, pp. 1065-1076, 12 pages.

Notice of Allowance received for U.S. Appl. No. 15/986,566 dated Nov. 3, 2020, 25 Pages.

Non-Final Office Action received for U.S. Appl. No. 15/986,579 dated Aug. 6, 2020, 36 pages.

Non-Final Office Action received for U.S. Appl. No. 15/986,566 dated Jul. 24, 2020, 33 pages.

Non-Final Office Action received for U.S. Appl. No. 15/986,598 dated Aug. 7, 2020, 36 pages.

List of IBM Patents or Applications to be treated as Related.

Non Final Office Action received for U.S. Appl. No. 15/986,617 dated May 25, 2022, 54 pages.

Baliki, et al., Corticostrialal functional connectivity predicts transition to chronic back pain, Nat Neurosci., Jul. 1, 2012; 15(8): 1117-9, doi: 10.1038/nn.3153.

Non Final Office Action received for U.S. Appl. No. 17/135,304 dated Oct. 14, 2022, 41 pages.

Non Final Office Action received for U.S. Appl. No. 17/134,686 dated Sep. 29, 2022, 44 pages.

Notice of Allowance received for U.S. Appl. No. 17/135,304 dated Feb. 10, 2023, 23 pages.

Notice of Allowance received for U.S. Appl. No. 17/134,686 dated Feb. 1, 2023, 23 pages.

\* cited by examiner

UPDATING A PRESCRIPTION STATUS BASED ON A MEASURE OF TRUST DYNAMICS

PARTIES TO A JOINT RESEARCH AGREEMENT

The present subject matter was developed and the claimed invention was made by or on behalf of Boston Scientific Neuromodulation Corporation and International Business Machines Corporation, parties to a joint research agreement that was in effect on or before the effective filing date of the claimed invention, and the claimed invention was made as a result of activities undertaken within the scope of the joint research agreement.

BACKGROUND

The subject disclosure relates to updating a status of a prescription (e.g. a medicine prescription), and more specifically, to autonomously updating a status of a prescription based on a trust dynamic measured using artificial intelligence technology.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses and/or computer program products that can autonomously update a status of a medicine prescription based on a trust dynamic measured using artificial intelligence technology are described.

According to an embodiment, a system is provided. The system can comprise a memory that can store computer executable components. The system can also comprise a processor, operably coupled to the memory, and that can execute the computer executable components stored in the memory. The computer executable components can comprise a prescription component that can update a status of a prescription associated with an entity based on a trust disposition value. The trust disposition value can be determined using machine learning technology and can be indicative of an expected effectiveness of the prescription.

According to an embodiment, a computer-implemented method is provided. The computer-implemented method can comprise updating, by a system operatively coupled to a processor, a status of a prescription associated with an entity based on a trust disposition value. The trust disposition value can be determined using machine learning technology and can be indicative of an effectiveness of the prescription.

According to an embodiment, a computer program product for autonomously updating a prescription is provided. The computer program product can comprise a computer readable storage medium having program instructions embodied therewith. The program instructions can be executable by a processor to cause the processor to update, by a system operatively coupled to the processor, a status of the prescription associated with an entity based on a trust disposition value. The trust disposition value can be determined using machine learning technology and can be indicative of an effectiveness of the prescription.

DETAILED DESCRIPTION

Figure 1:
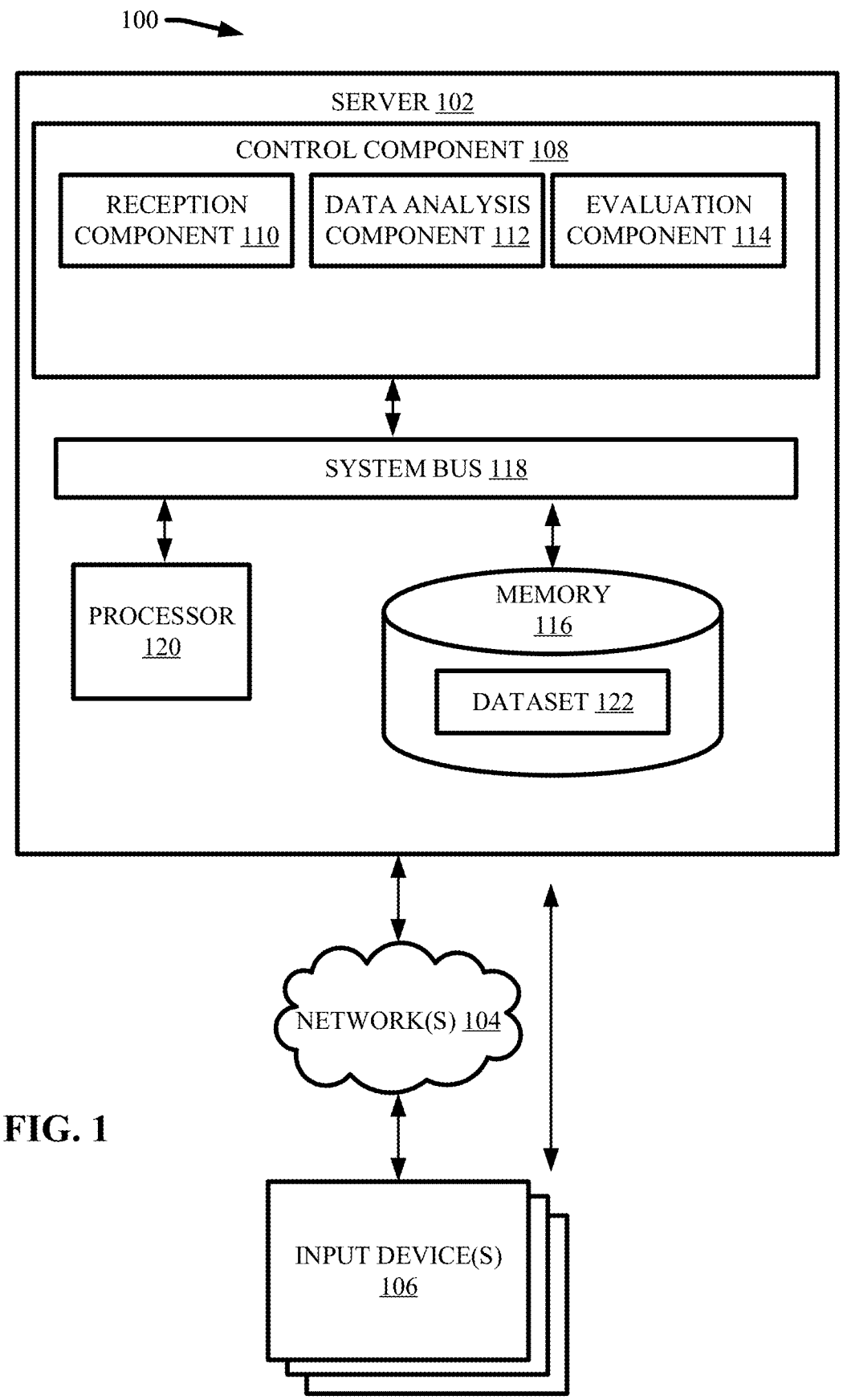
FIG. 1 illustrates a block diagram of an example, non-limiting system that can determine a trust disposition value regarding an entity associated with a prescription in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Many medicines are conventionally distributed to patients via a medicine prescription. The medicine prescription is written by a medical professional (e.g., a doctor) and can be taken to a medicine distributor (e.g., a pharmacy) by the patient. The medicine distributor can then distribute one or more medicines to the patient in accordance with the medicine prescription. Similarly, updates to the medicine prescription (e.g., renewals and/or changes in dosage of the medicine) require approval of a medical professional, which typically requires another medical assessment of the patient by the medical professional. For example, medicines having the possibility to cause substantial side effects (e.g., chemical dependency) typically require strict supervision by a medical professional to update associated medicine prescriptions.

Various embodiments of the present invention can be directed to computer processing systems, computer-implemented methods, apparatus and/or computer program products that facilitate the efficient, effective, and autonomous (e.g., without direct human guidance) updating of a status of a medicine prescription (e.g., renewal of the medicine prescription) using artificial intelligence ("AI") technology. For instance, one or more embodiments described herein can exploit a relationship between an entity's trust and an effectiveness of a medicine regarding the entity, thereby providing a window into the entity's likely responsiveness to the medicine. For example, wherein a medicine is used to manage pain, a measure of the entity's trust can be an indication of the entity's likely subjective experience of pain while using the medicine. Therefore, one or more embodiments can use a relationship between medicine effectiveness and trust dynamics of the entity (e.g., the patient) to autonomously update a status of a medicine prescription (e.g., renew the medical prescription, fail to renew the medicine prescription, and/or change a dosage of medicine associated with the medicine prescription).

For example, in one or more embodiments described herein can regard measuring, via one or more AI technologies, a trust dynamic associated with an entity (e.g., a patient) and/or can update a medicine prescription based on the measured trust dynamic. Measuring the trust dynamic can be achieved by analyzing one or more electronic communications, wherein commitments regarding the entity can be identified and found to be fulfilled and/or unfulfilled. The trust dynamic can be indicative of the entity's responsiveness to a medicine. Further, various embodiments can autonomously update the status of a prescription regarding the medicine and the entity based on the trust dynamic.

The computer processing systems, computer-implemented methods, apparatus and/or computer program products employ hardware and/or software to solve problems that are highly technical in nature (e.g., updating a prescription based on one or more analytically computed trust disposition values that can characterize one or more trust dynamics associated with an entity), that are not abstract and cannot be performed as a set of mental acts by a human. For example, an individual, or even a plurality of individuals, cannot readily collect, maintain, and/or analyze vast volumes of data as expeditiously and/or efficiently as the various embodiments described herein. Additionally, one or more embodiments described herein can utilize AI technologies that are autonomous in their nature to facilitate determinations and/or predictions that cannot be readily performed by a human.

Within a patient's brain, correlations can be found between various ailments affecting the patient and one or more trust dynamics. For example, a correlation can exist between chronic pain and a patient's disposition to trust (e.g., in a medical professional and/or in a medicine). As used herein, the term "pain" can refer to an unpleasant sensory and/or emotional experience associated with actual or potential tissue damage. Also, as used herein, the term "chronic pain" can refer to pain that persists past a healing period, having widespread effects that can influence one or more levels of a nervous system. Chronic pain can persist for greater than or equal to three months and/or can significantly impact a person's psychological well-being.

In 2010, the American Academy of Pain Medicine ("AAPM") estimated that over 100 million Americans suffer from a chronic pain condition, and said conditions can cos the United States over 500 billion dollars annually from health care costs and/or lost productivity. Diagnosing and/or treating chronic pain conditions can be difficult clinical tasks and/or can be further complicated by patient-physician dynamics, such as trust preservation over the course of the client-practitioner relationship.

Chronic pain and trust, while being distinct experiences, can have considerable overlap physiologically and/or psychologically. For example, from a neuroscience perspective, both phenomena can rely on some of the same brain regions and/or similar brain networks involved in emotional processing, emotional regulation, interoceptive awareness, memory consolidation, memory recall, decision making, and/or social attribution learning. The subject brain portions can include, for example: the insula, the anterior cingulate cortex ("ACC"), the posterior cingulate cortex, the hippocampus, the amygdala, and/or the frontal cortices (e.g., the medial prefrontal cortex ("mPFC")). Evidence of the shared neurocircuitry between aliments (e.g., chronic pain) and trust can be found both at a structural level (e.g., by analyzing grey and/or white mater properties within a patient's brain) and/or at a neurophysiological level (e.g., by analyzing functional connects between brain regions while a patient is at rest and/or performing a task). Due at least to the described correlations, a patient's level of trust can interact and/or influence their ailment (e.g., chronic pain), including responsiveness to a treatment regarding the ailment.

Furthermore, ailments, such as pain, and trust can have aspects of trait-like and/or state-like qualities, which can be considered when analyzing trust dynamics of a patient. Regarding trait-like qualities, a patient's brain structure (e.g., grey matter density, volume, the shape of subcortical regions, and/or the number of white matter connections) can facilitate predicting the patient's likelihood of developing an ailment (e.g., chronic pain). Also, functional connectivity between nucleus accumbens and/or the mPFC can facilitate predicting one or more transitions between states of the ailment (e.g., a transition from acute pain to chronic pain). Thus, a patient's brain structure can predispose the patient to a have an increased likelihood of suffering from the ailment (e.g., chronic pain), even before a triggering event (e.g., an injury).

Similarly, a patient's brain structure can also facilitate in predicting individual differences in preconscious evaluation of another's trustworthiness (e.g., gray matter volume of the mPFC can be correlated to a perceived untrustingness of others). For example, diffusion-tensor imaging ("DTI") can show differences in functional anisotropy ("FA") measures of white matter tract integrity around brain regions involved in social cognition between individuals with normal vs impaired perceptions of trustworthiness. Since structural properties of gray matter and white matter do not change drastically in short time frames, such imaging suggest that individuals may be predisposed in the extent to which they can trust a person and/or situation.

Regarding state-like qualities, both trust and one or more ailments (e.g., chronic pain) can be non-stationary over time (e.g., due to a patient's life experiences in combination with their underlying neuropsychological pre-dispositions). Also, the strength of functional connectivity between the dorsomedial prefrontal cortex ("dmPFC") and the ACC and/or between the insula and the hippocampus can change as a function of perceived trustworthiness. Further, empathy towards another's ailment (e.g., pain) can be shaped by perceived trustworthiness and reflected in modulated neural processing with reduced activations of emotional processing regions when observing someone less trustworthy. Trust can also be affected by the patient's current emotional state and/or mood. Similarly, some aliments (e.g., pain) can have dynamic properties such as: varying durations, varying intensities, and/or varying perceived locations. For example, long lasting ailments (e.g., chronic pain) can fluctuate about a mean intensity and/or exhibit peaks in intensity due to external triggers. For instance, neuroimaging can show that dynamics in subjective pain ratings can be reflected in the functional connectivity of sensory and/or emotional brain networks. Also, neurophysiological activity can change as a function of the intensity of pain and/or effectiveness of a medication, even a placebo. Further, like trust, a patient's mood can impact the severity of an ailment (e.g., severity of pain) perceived by a patient. Thus, in addition to predisposing factors, one or more ailments (e.g., pain) and trust can both produce dynamics that can be tracked in time and linked to internal and/or external perturbations. Moreover, one or more ailments (e.g., chronic pain) and trust can share temporal, affective, and/or social contexts. For example, both phenomena can increase with age (e.g., older individuals can be more likely to suffer from chronic pain and can be more trusting).

Thus, trust can play a significant role in any successful therapeutic interaction and/or relationship. For example, in the case of chronic pain management, the ability to trust can influence the effectiveness of pain relief medications. Factors potentially involved in trust dynamics between a patient and a physician can span previous experiences, current contexts, and/or expected future occurrences. Example factors that can influence a physician's trust for a patient can include, but are not limited to: the patient's subjective report and/or overall demeanor, the patient's potential motives to seek treatment, the patient's potential level of responsibility, previous experience with patients suffering from the same ailment, discussions with colleagues who may or may not have referred the patient, and/or medical culture at the time. Example factors that can influence a patient's trust for a physician can include, but are not limited to: the physician's interpersonal interaction with the patient, the physician's reputation, whether the physician's prescribed advice and/or therapy makes the patient feel better, previous experience with other physicians, previous experience with similar treatments for the ailment, previous experience with different treatment for the ailment.

The claims and scope of the subject application, and any continuation, divisional or continuation-in-part applications claiming priority to the subject application, exclude embodiments (e.g., systems, apparatus, methodologies, computer program products and computer readable storage media) directed to implanted electrical stimulation for pain treatment and/or management.

FIG. 1 illustrates a block diagram of an example, non-limiting system 100 that can update a medicine prescription based on a determined trust disposition value in accordance with one or more embodiments described herein. Repetitive description of like elements employed in other embodiments described herein is omitted for sake of brevity. Aspects of systems (e.g., system 100 and the like), apparatuses or processes in various embodiments of the present invention can constitute one or more machine-executable components embodied within one or more machines, e.g., embodied in one or more computer readable mediums (or media) associated with one or more machines. Such components, when executed by the one or more machines, e.g., computers, computing devices, virtual machines, etc. can cause the machines to perform the operations described.

As shown in FIG. 1, the system 100 can comprise one or more servers 102, one or more networks 104, and/or one or more input devices 106. The server 102 can comprise control component 108. The control component 108 can further comprise reception component 110, data analysis component 112, and/or evaluation component 114. Also, the server 102 can comprise or otherwise be associated with at least one memory 116. The server 102 can further comprise a system bus 118 that can couple to various components such as, but not limited to, the control component 108 and associated components, memory 116 and/or a processor 120. While a server 102 is illustrated in FIG. 1, in other embodiments, multiple devices of various types can be associated with or comprise the features shown in FIG. 1. Further, the server 102 can communicate with a cloud computing environment via the one or more networks 104.

The one or more networks 104 can comprise wired and wireless networks, including, but not limited to, a cellular network, a wide area network (WAN) (e.g., the Internet) or a local area network (LAN). For example, the server 102 can communicate with the one or more input devices 106 (and vice versa) using virtually any desired wired or wireless technology including for example, but not limited to: cellular, WAN, wireless fidelity (Wi-Fi), Wi-Max, WLAN, Bluetooth technology, a combination thereof, and/or the like. Further, although in the embodiment shown the control component 108 can be provided on the one or more servers 102, it should be appreciated that the architecture of system 100 is not so limited. For example, the control component 108, or one or more components of control component 108, can be located at another computer device, such as another server device, a client device, etc.

The one or more input devices 106 can comprise one or more computerized devices, which can include, but are not limited to: personal computers, desktop computers, laptop computers, cellular telephones (e.g., smart phones), computerized tablets (e.g., comprising a processor), smart watches, keyboards, touch screens, mice, a combination thereof, and/or the like. A user of the system 100 can utilize the one or more input devices 106 to input data into the system 100, thereby sharing (e.g., via a direct connection and/or via the one or more networks 104) said data with the server 102. For example, the one or more input devices 106 can send data to the reception component 110 (e.g., via a direct connection and/or via the one or more networks 104). Additionally, the one or more input devices 106 can comprise one or more displays that can present one or more outputs generated by the system 100 to a user. For example, the one or more displays can include, but are not limited to: cathode tube display ("CRT"), light-emitting diode display ("LED"), electroluminescent display ("ELD"), plasma display panel ("PDP"), liquid crystal display ("LCD"), organic light-emitting diode display ("OLED"), a combination thereof, and/or the like.

In one or more embodiments, the control component 108 can analyze data (e.g., including data entered into the system 100 via the one or more input devices 106) to determine a trust disposition value using one or more machine learning technologies. As used herein, the term "machine learning technologies" can refer to an application of AI technologies to automatically learn and/or improve from an experience (e.g., training data) without explicit programming of the lesson learned and/or improved. Also, as used herein, the term "trust disposition value" can refer to a numerical value that can represent an entity's current likeliness to trust another individual, medicine, medical treatment, therapy, and/or situation.

Typical approaches in defining and/or estimating trust can be classified as conceptual approaches and/or computational approaches. Conceptual approaches can consider the intuitive aspects of trust. For example, a person providing the trust ("a trustor") can be vulnerable to decisions made by a person receiving said trust ("a trustee"). However, conceptual approaches lack a means to compute a trust disposition value that can represent said intuitive aspects of trust. Conventional computational approaches can compute a trust value, but are domain-specific and emphasize numerical heuristics, thereby ignoring the intuitiveness behind trust. In one or more embodiments, the control component 108 can bridge the gap between the typical conceptual and computational approaches by determining a trust disposition value based on one or more commitments. For example, the one or more commitments can be represented as "C(debtor, creditor, antecedent, consequent)," wherein the debtor can commit to bring about the consequent for the creditor provided the antecedent holds. For instance "C(physician, patient, visiting the physician, providing a medical report)" can be an exemplary commitment, wherein: the physician can be debtor, the patient can be the creditor, the antecedent can be visiting the physician, and/or the consequent can be providing a medical report. When the physician provides the medical report, the example commitment is satisfied. If the physician fails to provide the medical report, the example commitment is violated. Thus, one or more commitments can, for example, capture social relationships between a physician and a patient, thereby providing a basis for computing trust between the entities. Based at least on data regarding one or more commitments, the control component 108 can utilize machine learning technologies to determine one or more trust disposition values.

The reception component 110 can receive the data entered by a user of the system 100 via the one or more input devices 106. The reception component 110 can be operatively coupled to the one or more input devices 106 directly (e.g., via an electrical connection) or indirectly (e.g., via the one or more networks 104). Additionally, the reception component 110 can be operatively coupled to one or more components of the server 102 (e.g., one or more component associated with the control component 108, system bus 118, processor 120, and/or memory 116) directly (e.g., via an electrical connection) or indirectly (e.g., via the one or more networks 104).

In various embodiments, the reception component 110 can utilize one or more AI technologies to identify and/or request data from an entity (e.g., a patient). For example, the reception component 110 can use one or more chatbots (e.g., a talkbot, a chatterbot, a chatterbox, and/or an artificial conversational entity) to facilitate one or more communications between the entity and the reception component 110 (e.g., via the one or more input devices 106 and/or the one or more networks 104). The one or more communications can regard one or more commitments involving the subject entity (e.g., patient). As used herein, the term "chatbot" can refer to a computer program that can conduct one or more conversations with an entity (e.g., a patient) via auditory and/or textual methods. The one or more chatbots can be designed to convincingly simulate how a human could converse, thereby passing the Turing test.

The one or more chatbots can use a sophisticated natural language processing system (e.g., such as such as IBM WATSON®, other purveyors of pre-build intents and/or dialogue flows, and/or like) and/or can scan for keywords within an input (e.g., entered via the one or more input devices 106) and pull a stored reply comprising the most matching keywords and/or most similar wording patterning from a database. For example, the one or more chatbots can function based on one or more rules. In another example, the one or more chatbots can use AI technology to understand language and/or continually learn from conversations.

One or more entities can use the one or more input devices 106 to interact with the reception component 110 (e.g., via the one or more networks 104) and provide data to the control component 108. The received data can regard one or more communications regarding a subject entity (e.g., a patient) and/or can be stored in one or more datasets 122. The one or more datasets 122 can be located in the memory 116 and/or in another location in a cloud computing environment (e.g., accessible via the one or more networks 104). For example, the one or more chatbots can inquire into one or more commitments involving the entity (e.g., the patient). For instance, the one or more chatbots can communicate regarding, for example: past experiences with a physician; past experiences with a subject medicine; past experiences with a treatment; expectations regarding a physician, medication, and/or treatment; a level of satisfaction with a subject physician, medication and/or treatment; and/or a perceived reputation of a subject physician, medication and/or treatment.

The data analysis component 112 can extract one or more features from the one or more datasets 122 and/or from one or more external sources (e.g., via the one or more networks 104). The extracted features can represent, for example, the debtor, the creditor, the antecedent, and/or the consequent of a subject commitment. In other words, the data analysis component 112 can analyze the data received and/or stored by the reception component 110 (e.g., via one or more chatbots) and extract one or more features that can represent one or more commitments involving the subject entity (e.g., subject patient).

Further, in one or more embodiments the data analysis component 112 can analyze data (e.g., electronic communications) regarding the entity from one or more external sources (e.g., data not entered via an engagement with the reception component 110). For example, a subject entity (e.g., a subject patient) can grant the data analysis component 112 access to one or more emails involving the entity. The data analysis component 112 can analyze the one or more emails to identify one or more commitments and/or extract one or more features regarding the one or more commitments.

The data analysis component 112 can use natural language processing to extract the one or more features, wherein the one or more features can be ngrams (e.g., unigrams and/or bigrams), modal verbs, action verbs, and/or deadline from one or more sentences of the conversations regarding the subject entity (e.g., via interaction with one or more chatbots and/or via communication with another individual, such as by email). Subsequently, the data analysis component 112 can train a classifier program (e.g., such as a support vector machine, a deep neural network, a random forest and/or decision forest, and/or like) based on the one or more extracted features.

In various embodiments, the evaluation component 114 can determine one or more commitment operations based on the one or more extracted features and/or generate one or more trust disposition values. The evaluation component 114 can represent trust as binary evidence "<r,s>;" wherein "r" can represent a positive experience involving the entity and can be greater than or equal to zero, and wherein "s" can represent a negative experience involving the entity and can be greater than or equal to zero. Thus, one or trust disposition values can be computed by the evaluation component 114 as the probability of a positive outcome, which can be represented by "a" as shown in Equation 1 below.

$$\alpha = \frac{r}{r+s} \quad \text{Equation 1}$$

The control component 108 (e.g., via the reception component 110, the data analysis component 112, and/or the evaluation component 114) can maintain evidence "<r,s>" about a subject entity (e.g., a patient), wherein an initial evidence, "<$r_{in}$, $s_{in}$>" can represent the entity's bias. One or more interactions between the entity and a physician, medicine, and/or medical treatment (e.g., as characterized by one or more commitments represented via one or more communications) can yield a positive, negative, or neutral experience. Thus, with each interaction (e.g., with each communication captured by the one or more chatbots and/or an external source such as email) the entity's initial evidence can be updated by adding "<$i_r$,0>", "<0,$i_s$>" and "<$\lambda i_r$, $(1-\lambda)i_s$>"; wherein $\lambda \in [0,1]$, wherein "$i_r$" can represent new evidence of a positive experience, and wherein "$i_s$" can represent new evidence of a negative experience. Therefore, the evaluation component 114 can determine an entity's trust disposition value based on at least the five parameters: "$i_r$", "$i_s$", "$r_{in}$", "$s_{in}$", and/or "$\lambda$." To learn the parameters based on positive experiences (e.g., represented by "$E^+$"), negative experiences (e.g., represented by "$E^-$"), and/or neutral experiences (e.g., represented by "E"), the evaluation component 114 can represent the trust disposition value in accordance with Equation 2 below.

$$\alpha = \frac{r_{in} + (i_r * E^+) + \lambda * i_r * E}{r_{in} + s_{in} + (i_r * E^+) + (i_s * E^-) + E(\lambda * i_r + (1-\lambda)i_s)} \quad \text{Equation 2}$$

For example, Table 1, provided below, can depict exemplary analysis (e.g., via the data analysis component 112) and/or evaluation (e.g., via evaluation component 114) of multiple email interactions (e.g., communications involving one or more commitments) involving an entity. As shown in Table 1, commitment operations can be determined based on one or more features extracted from the emails. The commitment operations can delineate, for example, that: a commitment has been created (e.g., represented by "create($C_1$)," which can indicate that a first commitment has been created, and/or by "create($C_2$)," which can indicate that a second commitment has been created); that a commitment has been fulfilled (e.g., represented by "satisfied ($C_1$);" and/or that a commitment has been violated (e.g., represented by "violate ($C_2$)."

TABLE 1

| Sender | Receiver | Email | Operation |
|---|---|---|---|
| Kim | Dorothy | I will check with Alliance Travel Agency . . . | create($C_1$) |
| Kim | Dorothy | I checked with our Travel Agency . . . | satisfied($C_1$) |
| Rob | Kim | By Wednesday, please send all copies of your documentation . . . | create($C_2$) |
| Kim | Rob | Rob, please forgive me for not sending . . . | violate($C_2$) |

Additionally, Table 2, presented below, can depict computed trust disposition values that can represent relationships of trust characterized by the exemplary email interactions depicted in Table 1. As shown in Table 1, there are two exemplary email interactions between Kim and Dorothy. As shown in Table 2, amongst the two said email interactions, Kim's trust in Dorothy remains neutral (e.g., represented by "E=2") at least because Dorothy has neither fulfilled a commitment (e.g., represented by "$E^+$=0") nor violated a commitment (e.g., represented by "$E^-$=0"). Also, as shown in Table 2, amongst the two email interactions between Kim and Dorothy, Dorothy's trust in Kim is positive at least because: the first email interaction created a commitment, and was thus neutral (e.g., represented by "E=1"), and the second email interaction fulfilled a commitment (e.g., represented by "$E^+$=1") without violating a commitment between the entities (e.g., represented by "$E^-$=0"). Further, as shown in Table 2: "S1-S5" can represent possible trust disposition values created by analyzing the communications and/or interactions between Kim and Dorothy.

TABLE 2

| Trust Pairs | Experiences | S1 | S2 | S3 | S4 | S5 |
|---|---|---|---|---|---|---|
| Kim → Dorothy | E = 2, $E^+$ = 0, $E^-$ = 0 | 0.45 | 0.6 | 0.8 | 0.6 | 0.56 |
| Dorothy → Kim | E = 1, $E^+$ = 1, $E^-$ = 0 | 0.7 | 0.9 | 0.8 | 0.76 | 0.84 |

One of ordinary skill in the art will recognize that while the exemplary data depicted in Table 1 and/or Table 2 can be derived from an external source (e.g., one or more email accounts), data analyzed and/or evaluated by the control component 108 (e.g., via the data analysis component 112 and/or the evaluation component 114) can be received through one or more communications with a subject entity by AI technology (e.g., one or more chatbots utilized by the reception component 110). Furthermore, while the exemplary data depicted in Table 1 and/or Table 2 depicts one or more trust relations (e.g., characterized by one or more trust disposition values) between two individuals (e.g., a patient/physician relationship), one or more trust disposition values can also characterize trust relations between an entity and an object (e.g., a medicine) and/or an event (e.g., medical treatment and/or therapy). For example, data received by the reception component 110 (e.g., via one or more chatbots) and/or analyzed by the data analysis component 112 can regard an entity's past experiences and/or future expectations regarding a medicine and/or medical treatment. For instance, one or more commitments comprised with the one or more communications can regard fulfillment and/or violation of results expected to be achieved by a medicine and/or medical treatment.

Thus, in various embodiments the control component 108 (e.g., via the reception component 110) can receive data representing one or more communications involving an entity (e.g., a patient). The received data can regard one or more commitments that can influence the entities disposition to provide trust. The control component 108 can determine one or more initial trust values (e.g., an initial trust disposition value) based on the data. Also, the control component 108 can extract one or more features from the data to train machine learning technologies, which can update the initial trust value to represent trust predictions that can characterize future trust relations involving the entity (e.g., updated trust disposition values). Thus, the control component 108 can determine a trust disposition value regarding one or more relationships involving an entity (e.g., a patient) and/or can update the trust disposition value as new data (e.g., communications involving the entity) is received (e.g., via the reception component 110 and/or an external source such as email correspondences). Furthermore, in one or more embodiments the control component 108 can maintain the currency of one or more of the trust disposition values by updating said trust disposition values based on the periodic collection of new data. For example, the reception component 110 can receive new data (e.g., via the one or more chatbots) and/or the data analysis component 112 can analyze new data at predefined periodic intervals (e.g., each day, each week, each month, and/or the like). Further the evaluation component 114 can update one or more trust disposition values based on the most recent data and/or data analysis (e.g., most recent extract features). In other words, the functions of the control component 108 can be repeated periodically to ensure the trust disposition values are up-to-date and accurately represent the current disposition of an entity.

Figure 2:
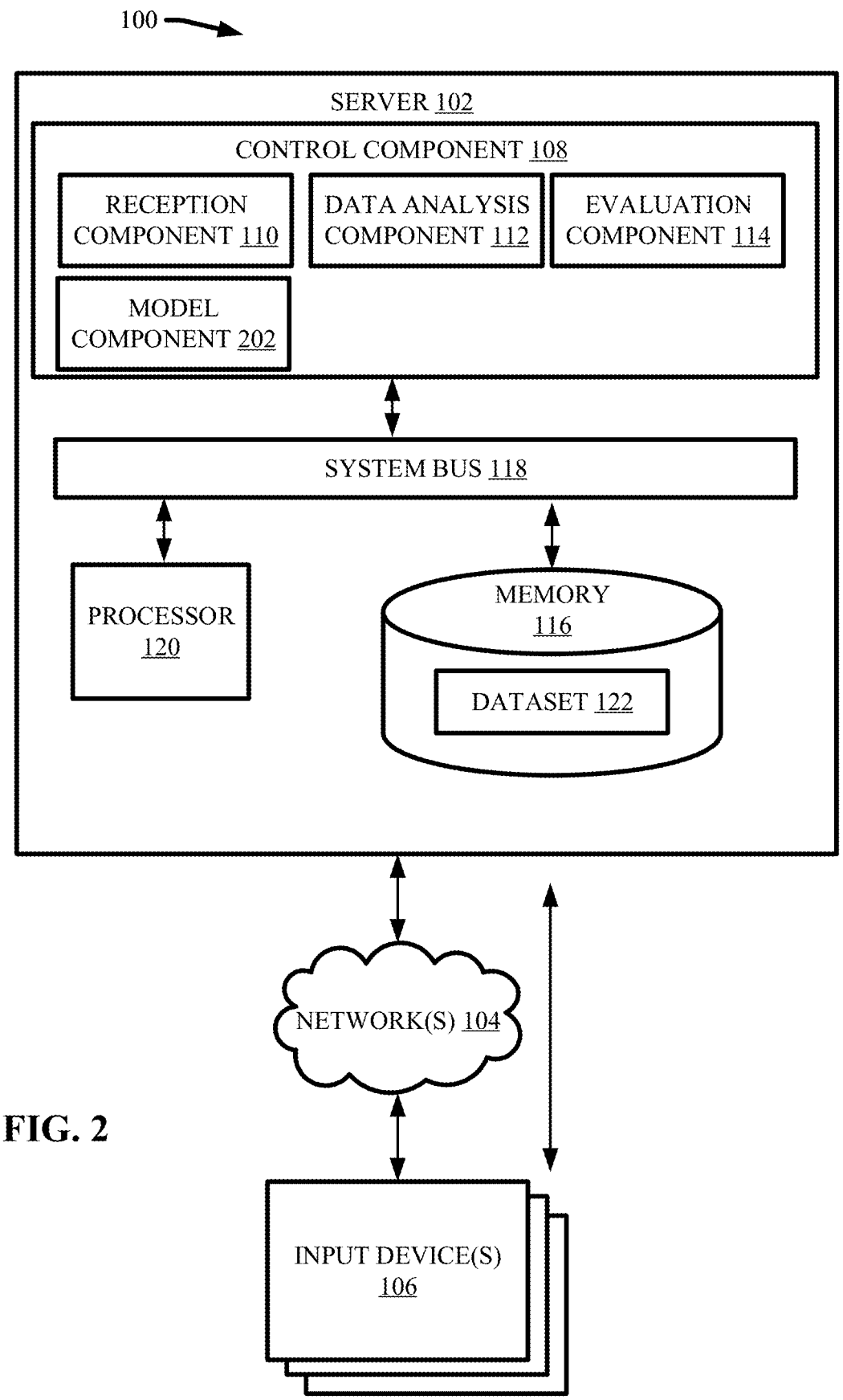
FIG. 2 illustrates a block diagram of an example, non-limiting system that can determine a trust disposition value regarding an entity associated with a prescription in accordance with one or more embodiments described herein.

FIG. 2 illustrates a block diagram of the example, non-limiting system 100 further comprising model component 202 in accordance with one or more embodiments described herein. Repetitive description of like elements employed in other embodiments described herein is omitted for sake of brevity.

The model component 202 can generate one or more trust graphs, which can facilitate determining trust disposition values regarding a new relationship involving the entity based on one or more trust disposition values regarding other relationships involving the entity. As used herein, the term "trust graph" can refer to a computer model that depicts linkages between individuals and/or objects (e.g., medicines and/or medical treatments) through which trust can be represented (e.g., via one or more trust disposition values) and/or traversed algorithmically. For example, one or more linkages of a trust graph can depict how a subject entity (e.g., a patient) can be indirectly correlated to a target individual and/or object through one or more intermediate individuals and/or objects. Further, trust disposition values associated with the subject entity and the one or more intermediate individuals and/or object can facilitate predicting a trust disposition value associated with an indirect relationship between the subject entity and the target individual and/or object, despite a lack of previous experience and/or communication between the subject entity and/or the target individual and/or object.

For instance, one or more trust graphs generated by the model component 202 can depict a direct linkage between Fred and Fred's friend Harry. Further, the one or more trust graphs can depict a high trust disposition value associated with the direct link between Fred and Harry, thereby indicating, for example, that Fred has a high disposition of trust towards Harry. Also, the one or more trust graphs can depict a direct linkage between Harry and Harry's doctor, Dr. Lou. Further, the one or more trust graphs can depict a high trust disposition value associated with the direct link between Harry and Dr. Lou, thereby indicating, for example, that Harry has a high disposition of trust towards Dr. Lou. Harry can refer Fred to Dr. Lou, wherein a trust disposition value regarding Fred's disposition of trust towards Dr. Lou can be predicted at least because Harry can act as an intermediary to establish an indirect linkage between Fred and Dr. Lou. Thus, the model component 202, via the one or more trust graphs, can predict that Fred has a high disposition of trust towards Dr. Lou despite no previous encounters between the two individuals based on the high disposition values associated with the direct linkages (e.g., the direct link between Fred and Harry and/or the direct link between Harry and Dr. Lou) that form the indirect link between Fred and Dr. Lou.

Thus, in various embodiments the model component 202 can predict one or more disposition values associated with one or more new relationships based on one or more disposition values associated with established relationships that have influenced the one or more new relationships. Wherein a subject relationship (e.g., between a patient and a physician, between a patient and a medicine, and/or between a patient and a medical treatment) is established through one or more intermediary relationships, a trust disposition value characterizing the subject relationship can be predicted (e.g., via the model component 202) based on one or more trust disposition values associated with the one or more intermediary relationships. In other words, the model component 202 can predict one or more trust disposition values associated with an indirect relationship (e.g., a relationship that can lack previous interaction between subject entities) based on one or more trust disposition values associated with one or more direct relationships (e.g., a relationship that can be characterized by past interactions, such as commitments, between the subject entities).

Figure 3:
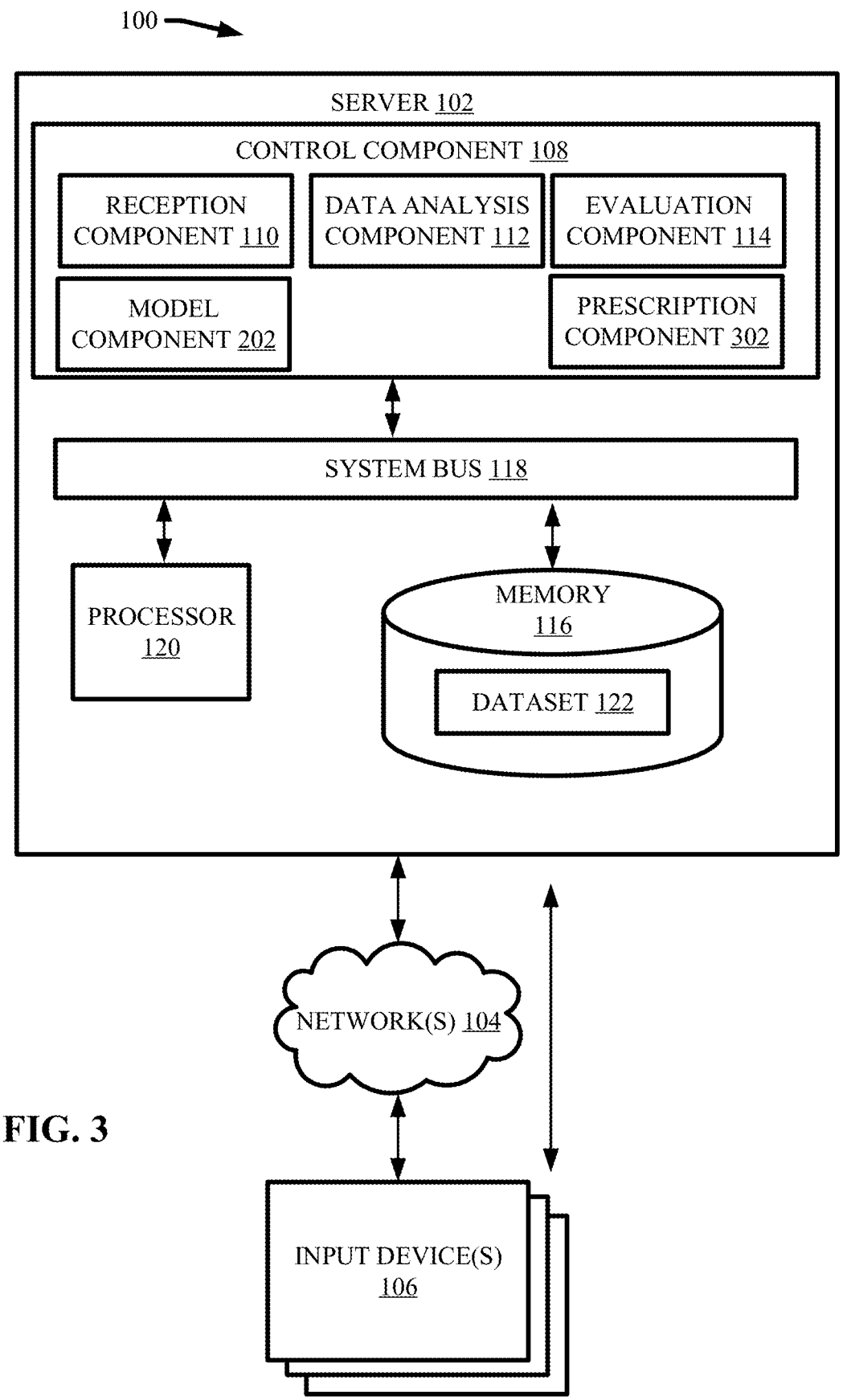
FIG. 3 illustrates a block diagram of an example, non-limiting system that can update the status of one or more prescriptions based on at least a trust disposition value regarding an entity associated with the one or more prescriptions in accordance with one or more embodiments described herein.

FIG. 3 illustrates a block diagram of the example, non-limiting system 100 further comprising prescription component 302 in accordance with one or more embodiments described herein. Repetitive description of like elements employed in other embodiments described herein is omitted for sake of brevity.

In various embodiments, the prescription component 302 can update a status of one or more medicine prescriptions based on one or more determined and/or predicted trust disposition values. As used herein, the term "medicine prescription" can refer to an authorization by one or more medical care givers (e.g., medical professionals such as physicians) for an entity to receive one or more medicines and/or medical treatments. Thus, a medicine prescription can authorize distribution of a medicine to an entity. The medicine prescription can delineate one or more features of a subject medicine and/or medical treatment. Example features that can be regarded by a medicine prescription can include, but are not limited to: one or more specific medicines to be distributed to the entity, one or more dosages of a subject medicine to be distributed to the entity, a frequency of distribution of a subject medicine and/or dosage to the entity, an amount of medicine to be distributed to an entity, a term of distribution of a medicine to an entity, a combination thereof, and/or the like. For example, a medicine prescription can indicate that an entity is authorized to receive a certain quantity of a specific medicine in a particular dosage at defined frequency (e.g., once). The status of a medicine prescription can regard one or more features of the medicine prescription. Further, an update to the status of a medicine prescription can comprise: changing one or more of the medicine prescription's features (e.g., a change to the frequency of distribution by enabling refills of the medicine prescription), and/or confirming one or more of the medicine prescription's features (e.g., failing to change one or more of the medicine prescription's features based on current information, such as a trust disposition value).

As discussed herein, an entity's (e.g., a patient) trust in an individual (e.g., a physician) and/or an object (e.g., a medicine and/or a medical treatment) can affect one or more responses the entity has regarding a service of the individual and/or object. For example, a patient's trust in his/her physician can influence the effectiveness of one or more medicines prescribed by the physician with regards to the patient. In another example, a patient's trust in his/her prescribed medicine can influence the effectiveness of the medicine. Thus, the one or more trust disposition values determined by the control component 108 (e.g., via the data analysis component 112, the evaluation component 114, and/or the model component 202) can be indicative of an expected effectiveness of one or more medicine prescriptions associated with the entity characterized by the one or more trust disposition values.

For example, wherein an entity has a large amount of trust in a medicine (e.g., due to one or more positive past experiences with the medicine and/or physician who prescribed the medicine), the medicine can demonstrate a high effectiveness in curing and/or treating an ailment of the entity. In another example, wherein the entity has a low amount of trust in a medicine (e.g., due to one or more negative past experiences with the medicine and/or physician who prescribed the medicine), the medicine can be less effective in curing and/or treating the same exemplary ailment.

In one or more embodiments, the prescription component 302 can autonomously update a status of one or more medicine prescriptions based on an entity's trust disposition value, wherein the trust disposition value can be indicative of an expected effectiveness of the medicine prescription. The prescription component 302 can update the status of the one or more medicine prescriptions based on, for example, whether the subject trust disposition value is greater than or less than a predefined threshold. For example, the prescription component 302 can update the status of the one or more medicine prescriptions such that the subject entity is authorized to receive more medicine when the trust disposition value indicates that the medicine is likely to be highly effective (e.g., when the trust disposition value is greater than a predefined threshold). For instance, the prescription component 302 can renew a medicine prescription based on a trust disposition value being greater than or equal to a predefined threshold. In another example, the prescription component 302 can update the status of the one or more medicine prescriptions such that the subject entity is authorized to receive less medicine when the trust disposition value indicates that the medicine is likely to be ineffective (e.g., when the trust disposition value is less than a predefined threshold). For instance, the prescription component 302 can confirm expiration of a medicine prescription based on a trust disposition value being less than or equal to a predefined threshold. In a further example, the prescription component 302 can update the status of the one or more medicine prescriptions to change the specific medicine addressed by the medicine prescription based on the one or more trust disposition values. For instance, wherein the model component 202 predicts a larger trust disposition value with regard to a different and equivalent medicine (e.g., a generic medicine) than the medicine authorized by the medicine prescription (e.g., a name-brand medicine), the prescription component 302 can change the medicine prescription to regard the different and equivalent medicine such that the entity is authorized to receive the medication that is most likely to be effective (e.g., based on the trust disposition values).

Thus, in one or more embodiments the prescription component 302 can change and/or confirm any of the feature of a medicine prescription based on one or more trust disposition values characterizing an entity associated with the medicine prescription. Additionally, the one or more medicine prescriptions can be stored in the memory 116 and/or a cloud computing environment accessible via the one or more networks 104.

Figure 4:
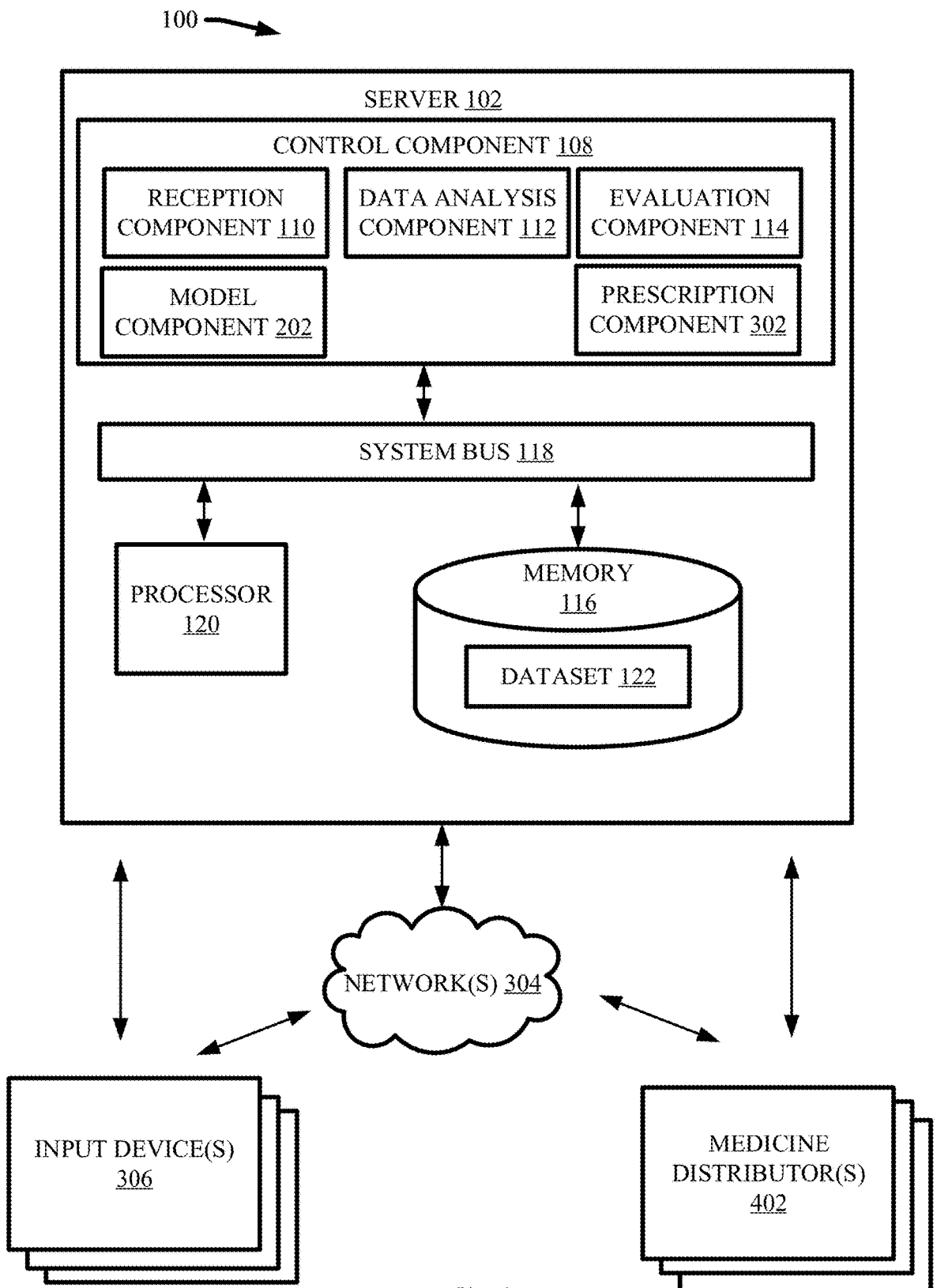
FIG. 4 illustrates a block diagram of an example, non-limiting system that can update the status of one or more prescriptions based on at least a determined trust disposition value and/or can inform one or more medical distributors of the updated status in accordance with one or more embodiments described herein.

FIG. 4 illustrates a block diagram of the example, non-limiting system 100 further comprising one or more medicine distributors 402 in accordance with one or more embodiments described herein. Repetitive description of like elements employed in other embodiments described herein is omitted for sake of brevity.

As shown in FIG. 4, the server 102 can be operatively coupled (e.g., directly and/or indirectly via the one or more networks 104) to one or more medicine distributors 402. The one or more medicine distributors 402 can distribute one or more medicines to an entity in accordance with a medicine prescription associated with the entity. Example medicine distributors 402 can include, but are not limited to: pharmacies, hospitals, licensed retailers, a combination thereof, and/or the like. In response to updating the status of medicine prescription, the prescription component 302 can send (e.g., automatically and/or at the request of a user of the system 100) the updated medicine prescription to the one or more medicine distributors 402. Alternatively, the one or more medical distributors can maintain one or more prescription databases comprising one or more medicine prescriptions associated with subject entity; wherein in response to updating the status of medicine prescription, the prescription component 302 can automatically update the one or more prescription databases.

Figure 5:
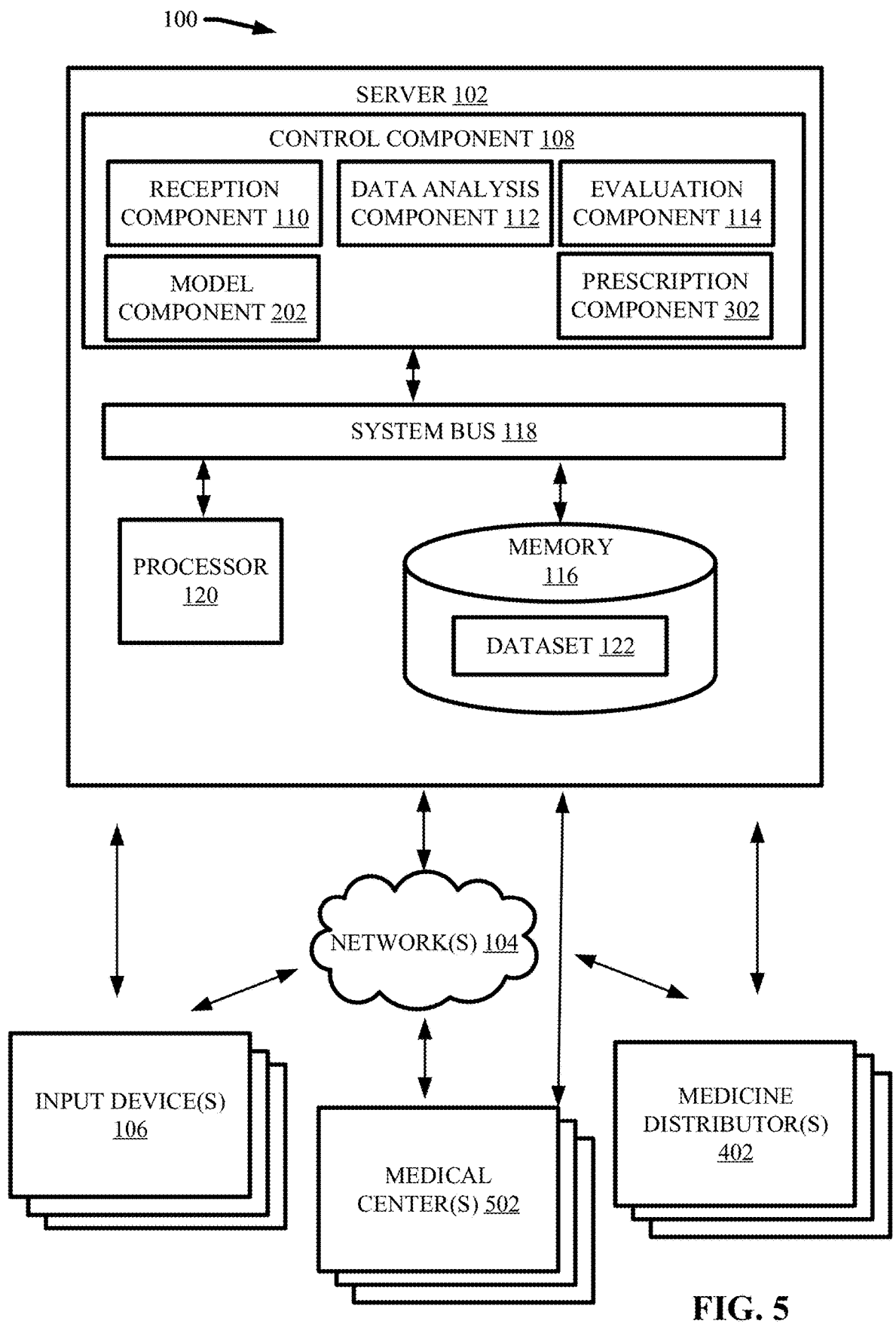
FIG. 5 illustrates a block diagram of an example, non-limiting system that can update the status of one or more prescriptions based on at least a trust disposition value and/or one or more medical diagnoses regarding an entity associated with the one or more medicine prescriptions in accordance with one or more embodiments described herein.

FIG. 5 illustrates a block diagram of the example, non-limiting system 100 further comprising one or more medical centers 502 in accordance with one or more embodiments described herein. Repetitive description of like elements employed in other embodiments described herein is omitted for sake of brevity.

As shown in FIG. 5, the server 102 can be operatively coupled (e.g., directly and/or indirectly via the one or more networks 104) to one or more medical centers 502. The one or medical centers 502 can be facilities where medical assistance, medical diagnoses, medical reports, medical therapies, and/or medical treatments can be provided. Example medical centers 502 can include, but are not limited to: hospitals, urgent care clinics, physician practices, nursing homes, a combination thereof, and/or the like. In one or more embodiments, the server 102 (e.g., the control component 108) can receive medical data from the one or more medical centers 502, wherein the medical data can regard a subject entity and can be used by the control component 108 to determine one or more trust disposition values. For example, one or more medical professionals (e.g., physicians) at the one or more medical centers 502 can capture images of a subject individual's brain structure to assess one or more neurological features. As previously described herein, an individual's brain structure can be indicative of the individual's predisposition to an ailment (e.g., pain and/or chronic pain) and/or willingness to trust. The medical data (e.g., one or more brain images and/or medical history) can be sent to the server 102 (e.g., the control component 108) and used (e.g., via the evaluation component 114) to create a predisposition baseline, which can be further augmented based on the other various forms of data described herein.

In various embodiments, the system 100 (e.g., via the control component 108) can autonomously: collect data regarding trust dynamics of an entity (e.g., data regarding communications that indicate the fulfillment or violation of one or more commitments); determine one or trust disposition values based on the collected data; maintain the currency of the one or more trust disposition values using, for example, one or more machine learning technologies; generate one or more trust graphs to predict one or more trust disposition values that can characterize indirect relationships involving the subject entity; update the status of one or more medicine prescriptions associated with the entity based on the one or more trust disposition values; and/or ensure that one or more medicine distributors 402 posses the one or more updated medicine prescriptions (e.g., by sending the updated medicine prescriptions and/or by modifying one or more prescription databases accessible by the one or more medicine distributors 402). Therefore, the system 100 tailor one or more medicine prescription associated to an entity based on recent experience involving the entity that can affect the entity's trust in the medicine prescription. Further, the system 100 can update the status of the one or more medicine prescription expeditiously by negating intervention by a medical professional (e.g., a physician). Thus, an individual subject to the analyses and/or evaluations of the system 100 can benefit from up-to-date medicine prescriptions that can be tailored to provide optimal effectiveness based on the individual's current disposition of trust.

Figure 6:
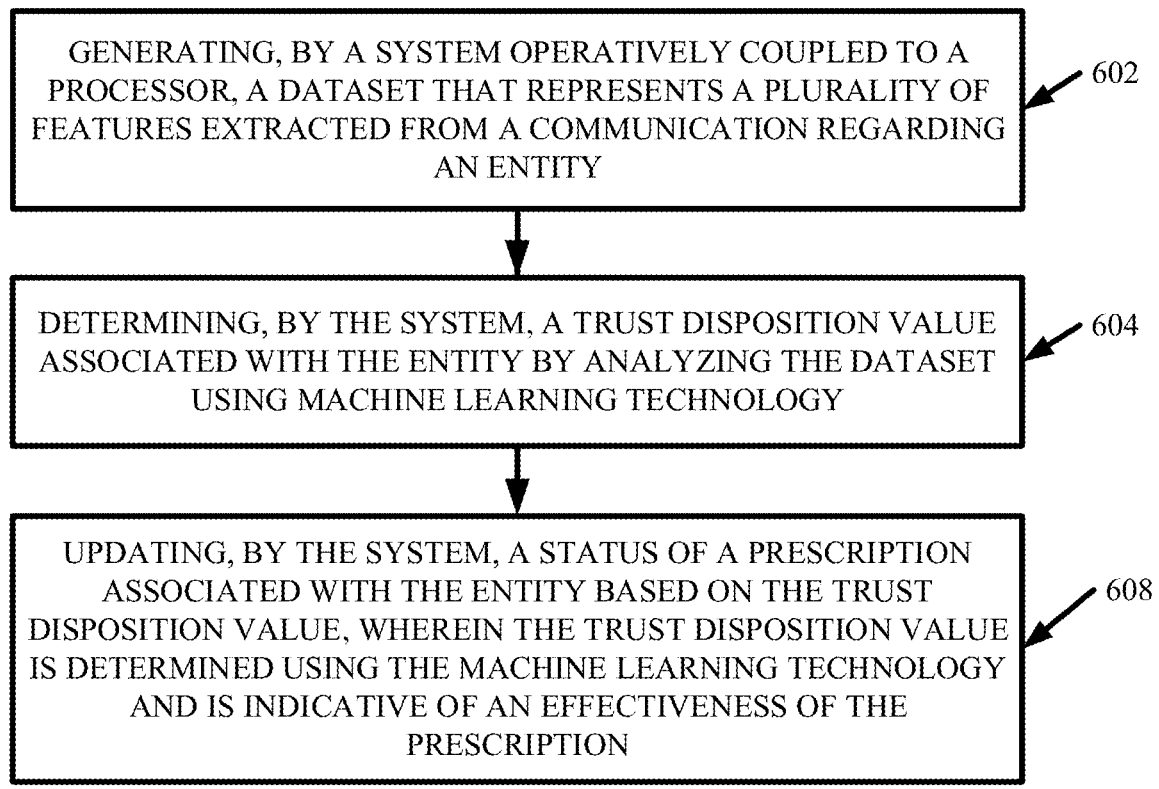
FIG. 6 illustrates a flow diagram of an example, non-limiting method that can facilitate updating a status of one or more prescriptions based on at least a trust disposition value regarding an entity associated with the one or more prescriptions in accordance with one or more embodiments described herein.

FIG. 6 illustrates a flow diagram of an example, non-limiting method 600 that can facilitate updating the status of one or more prescriptions (e.g., medicine prescriptions) based on one or more computed trust disposition values in accordance with one or more embodiments described herein. Repetitive description of like elements employed in other embodiments described herein is omitted for sake of brevity.

At 602, the method 600 can comprise generating, by a system 100 (e.g., via reception component 110 and/or data analysis component 112) operatively coupled to a processor 120, one or more datasets (e.g., dataset 122) that can represent a plurality of features extracted from one or more communications regarding an entity (e.g., a patient). In one or more embodiments, the one or more communications can be initiated and/or facilitated by one or more AI systems (e.g., one or more chatbots). Additionally, the one or more communications can be accessed via an external source, such as an email account. Further, the one or more communications can regard one or more commitments involving the entity, and/or the one or more extracted features can delineate whether the one or more commitments were fulfilled or violated. Thus, in various embodiments the one or more communications can be indicative of the entity's past positive and/or negative experiences with an individual (e.g., a physician) and/or object (e.g., a medicine and/or medical treatment).

At 604, the method 600 can comprise determining, by the system 100 (e.g., via the data analysis component 112 and/or the evaluation component 114), one or more trust disposition values associated with the entity by analyzing the one or more datasets using machine learning technology. For example, the determining can comprise computing a likelihood that the entity will trust an individual (e.g., a physician) and/or object (e.g., a medicine and/or medical treatment) based on past positive and/or negative experiences. For instance, the system 100 (e.g., via the evaluation component 114) can utilize Equation 1 and/or Equation 2 to compute the one or more trust disposition values.

At 606, the method 600 can comprise updating, by the system 100 (e.g., via the prescription component 302), a status of a prescription (e.g., a medicine prescription) associated with the entity based on the one or more trust disposition values, wherein the one or more trust disposition values can be determined using machine learning technology and be indicative of an effectiveness of the prescription. For example, the updating at 606 can be based on whether the one or more trust disposition values determined at 604 are greater than or less than a predefined threshold. Further, the updating can comprise changing and/or confirming one or more features of the medicine prescription. Example updates can include but are not limited to: changing the number of refills permitted by the medicine prescription, changing the expiration date of the medicine prescription, changing the dosage of a medicine addressed by the medicine prescription, changing the specific medicine addressed by the medicine prescription, a combination thereof, and/or the like.

Figure 7:
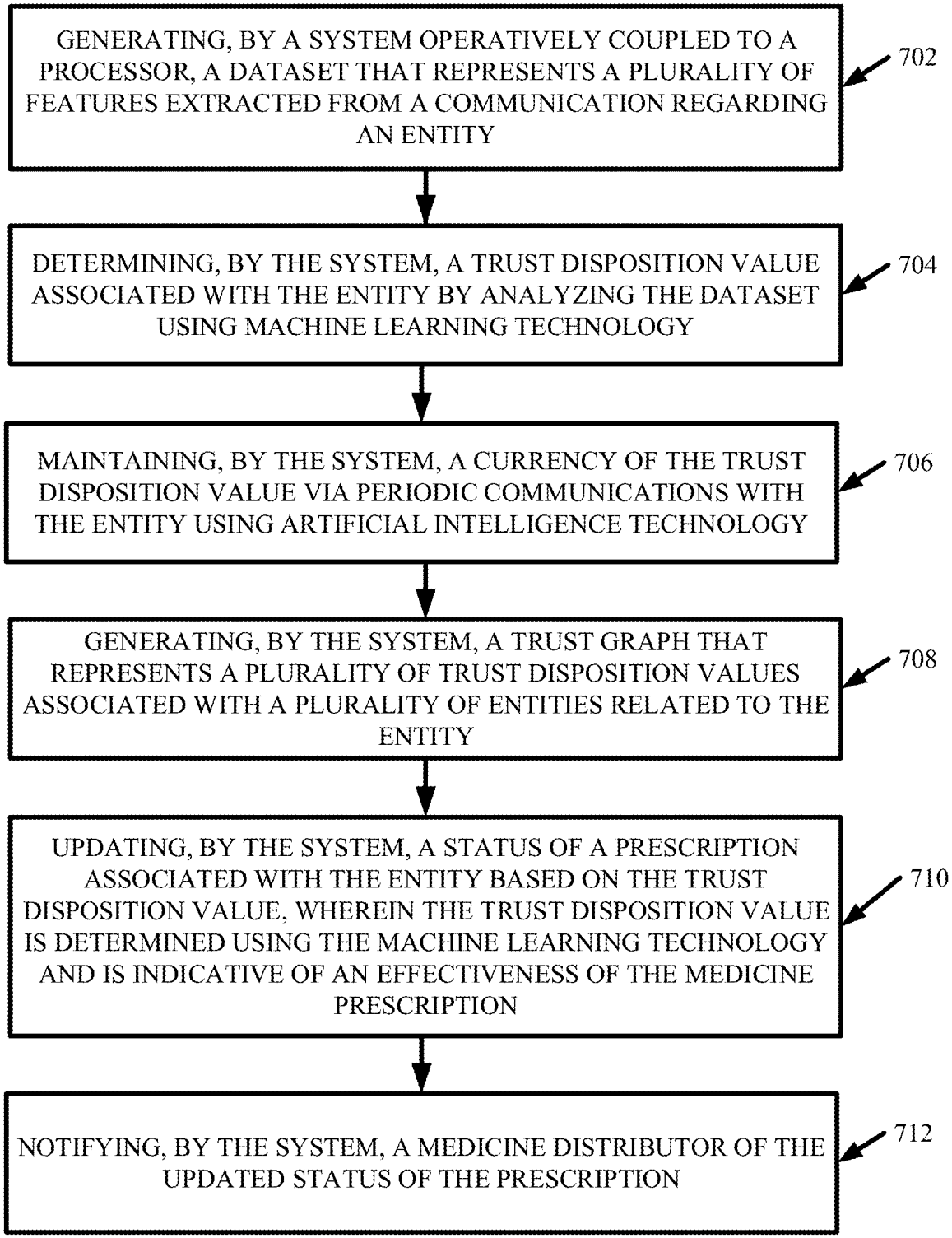
FIG. 7 illustrates a flow diagram of an example, non-limiting method that can facilitate updating a status of one or more prescriptions based on at least a trust disposition value regarding an entity associated with the one or more prescriptions in accordance with one or more embodiments described herein.

FIG. 7 illustrates a flow diagram of an example, non-limiting method 700 that can facilitate updating the status of one or more prescriptions (e.g., medicine prescriptions) based on one or more computed trust disposition values in accordance with one or more embodiments described herein. Repetitive description of like elements employed in other embodiments described herein is omitted for sake of brevity.

At 702, the method 700 can comprise generating, by a system 100 (e.g., via reception component 110 and/or data analysis component 112) operatively coupled to a processor 120, one or more datasets (e.g., dataset 122) that can represent a plurality of features extracted from one or more communications regarding an entity (e.g., a patient). In one or more embodiments, the one or more communications can be initiated and/or facilitated by one or more AI systems (e.g., one or more chatbots). Additionally, the one or more communications can be accessed via an external source, such as an email account. Further, the one or more communications can regard one or more commitments involving the entity, and/or the one or more extracted features can delineate whether the one or more commitments were fulfilled or violated. Thus, in various embodiments the one or more communications can be indicative of the entity's past positive and/or negative experiences with an individual (e.g., a physician) and/or object (e.g., a medicine and/or medical treatment).

At 704, the method 700 can comprise determining, by the system 100 (e.g., via the data analysis component 112 and/or the evaluation component 114), one or more trust disposition values associated with the entity by analyzing the one or more datasets using machine learning technology. For example, the determining can comprise computing a likelihood that the entity will trust an individual (e.g., a physician) and/or object (e.g., a medicine and/or medical treatment) based on past positive and/or negative experiences. For instance, the system 100 (e.g., via the evaluation component 114) can utilize Equation 1 and/or Equation 2 to compute the one or more trust disposition values.

At 706, the method 700 can comprise maintaining, by the system 100 (e.g., via the reception component 110, the data analysis component 112, and/or the evaluation component 114), a currency (e.g., a currentness) of the one or more trust disposition values via periodic communications with the entity using one or more AI technologies. For example, one or more chatbots (e.g., utilized by the reception component 110) can engage the entity in conversation in predefined intervals (e.g., each day, each week, each month, and/or the like). Further, the one or more trust disposition values can be updated (e.g., via the evaluation component 114) based on new data extracted (e.g., via the data analysis component 112) from the most current conversation with the chatbot.

At 708, the method 700 can comprise generating, by the system 100 (e.g., via the model component 202), one or more trust graphs that can represent a plurality of trust disposition values associated with a plurality of entities related to the entity. The plurality of entities can be in direct relationships with the entity or indirect relationships with the entity (e.g., relationships established through one or more intermediate relationships). The one or more trust graphs can facilitate determining one or more trust disposition values regarding relationships that lack historical data (e.g., lack communications between the subject entities and/or previous commitments between the entities).

At 710, the method 700 can comprise updating, by the system 100 (e.g., via the prescription component 302), a status of a prescription (e.g., a medicine prescription) associated with the entity based on the one or more trust disposition values, wherein the one or more trust disposition values can be determined using machine learning technology and be indicative of an effectiveness of the medicine prescription. For example, the updating at 710 can be based on whether the one or more current trust disposition values are greater than or less than a predefined threshold. Further, the updating can comprise changing and/or confirming one or more features of the medicine prescription. Example updates can include but are not limited to: changing the number of refills permitted by the medicine prescription, changing the expiration date of the medicine prescription, changing the dosage of a medicine addressed by the medicine prescription, changing the specific medicine addressed by the medicine prescription, a combination thereof, and/or the like.

At 712, the method 700 can comprise notifying, by the system 100 (e.g., via the prescription component 302), one or more medicine distributors 402 of the updated status of the prescription (e.g., the updated medical prescription). The notifying can comprise sending the updated prescription to the one or more medicine distributors 402 (e.g., via the one or more networks 104). Additionally, and/or alternatively, the notifying can comprise modifying data comprised within a prescription database, which is accessible and/or maintained by the one or more medicine distributors 402, to reflect the updated status of the prescription.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
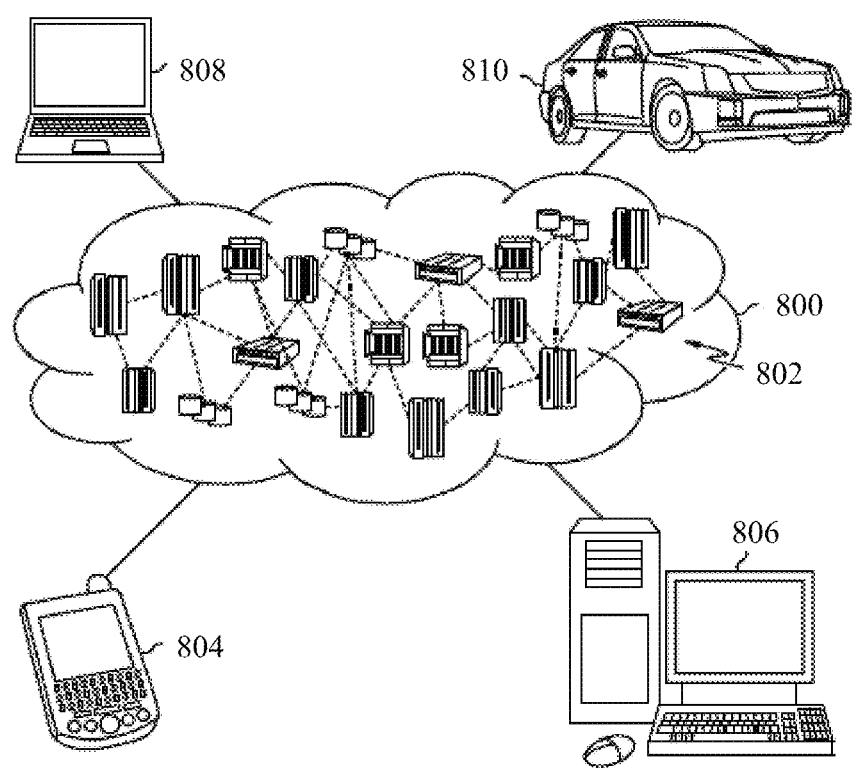
FIG. 8 depicts a cloud computing environment in accordance with one or more embodiments described herein.

Referring now to FIG. 8, illustrative cloud computing environment 800 is depicted. Repetitive description of like elements employed in other embodiments described herein is omitted for sake of brevity. As shown, cloud computing environment 800 includes one or more cloud computing nodes 802 with which local computing devices used by cloud consumers, such as, for example, personal digital assistant (PDA) or cellular telephone 804, desktop computer 806, laptop computer 808, and/or automobile computer system 810 may communicate. Nodes 802 may communicate with one another. They may be grouped (not shown) physically or virtually, in one or more networks, such as Private, Community, Public, or Hybrid clouds as described hereinabove, or a combination thereof. This allows cloud computing environment 800 to offer infrastructure, platforms and/or software as services for which a cloud consumer does not need to maintain resources on a local computing device. It is understood that the types of computing devices 804-810 shown in FIG. 8 are intended to be illustrative only and that computing nodes 802 and cloud computing environment 800 can communicate with any type of computerized device over any type of network and/or network addressable connection (e.g., using a web browser).

Figure 9:
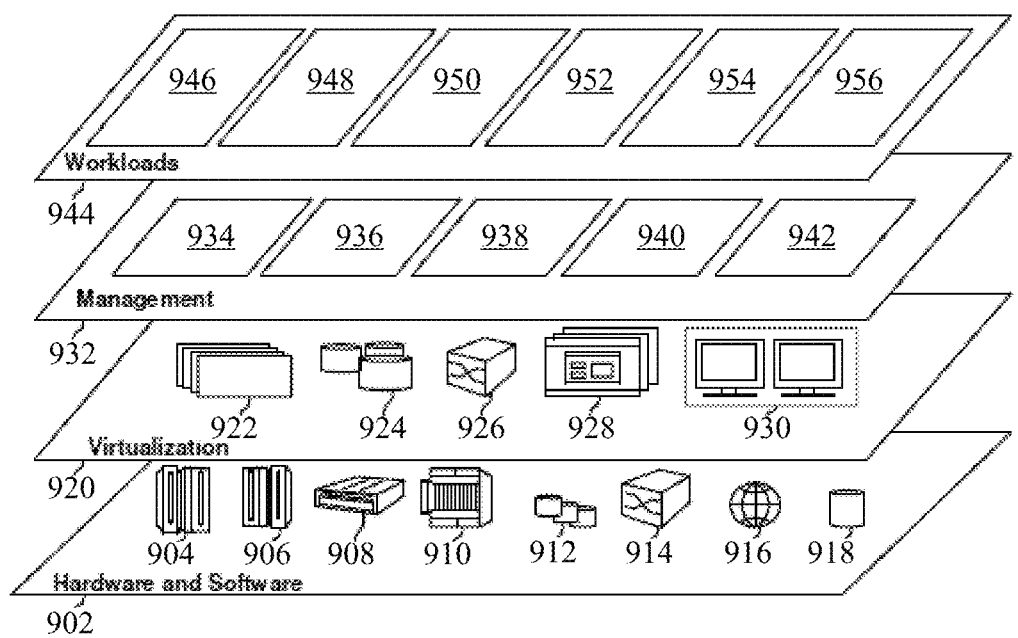
FIG. 9 depicts abstraction model layers in accordance with one or more embodiments described herein.

Referring now to FIG. 9, a set of functional abstraction layers provided by cloud computing environment 800 (FIG. 8) is shown. Repetitive description of like elements employed in other embodiments described herein is omitted for sake of brevity. It should be understood in advance that the components, layers, and functions shown in FIG. 9 are intended to be illustrative only and embodiments of the invention are not limited thereto. As depicted, the following layers and corresponding functions are provided.

Hardware and software layer 902 includes hardware and software components. Examples of hardware components include: mainframes 904; RISC (Reduced Instruction Set Computer) architecture based servers 906; servers 908; blade servers 910; storage devices 912; and networks and networking components 914. In some embodiments, software components include network application server software 916 and database software 918.

Virtualization layer 920 provides an abstraction layer from which the following examples of virtual entities may be provided: virtual servers 922; virtual storage 924; virtual networks 926, including virtual private networks; virtual applications and operating systems 928; and virtual clients 930.

In one example, management layer 932 may provide the functions described below. Resource provisioning 934 provides dynamic procurement of computing resources and other resources that are utilized to perform tasks within the cloud computing environment. Metering and Pricing 936 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 938 provides access to the cloud computing environment for consumers and system administrators. Service level management 940 provides cloud computing resource allocation and management such that required service levels are met. Service Level Agreement (SLA) planning and fulfillment 942 provide pre-arrangement for, and procurement of, cloud computing resources for which a future requirement is anticipated in accordance with an SLA.

Workloads layer 944 provides examples of functionality for which the cloud computing environment may be utilized. Examples of workloads and functions which may be provided from this layer include: mapping and navigation 946; software development and lifecycle management 948; virtual classroom education delivery 950; data analytics processing 952; transaction processing 954; and updating a prescription (e.g., a medicine prescription) status 956. Various embodiments of the present invention can utilize the cloud computing environment described with reference to FIGS. 8 and 9 to determine a trust disposition value associated with one or more entities and/or update the status of a prescription associated with the one or more entities based on the trust disposition value.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing.

A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware based systems that perform the specified functions or acts or carry out combinations of special purpose hardware and computer instructions.

Figure 10:
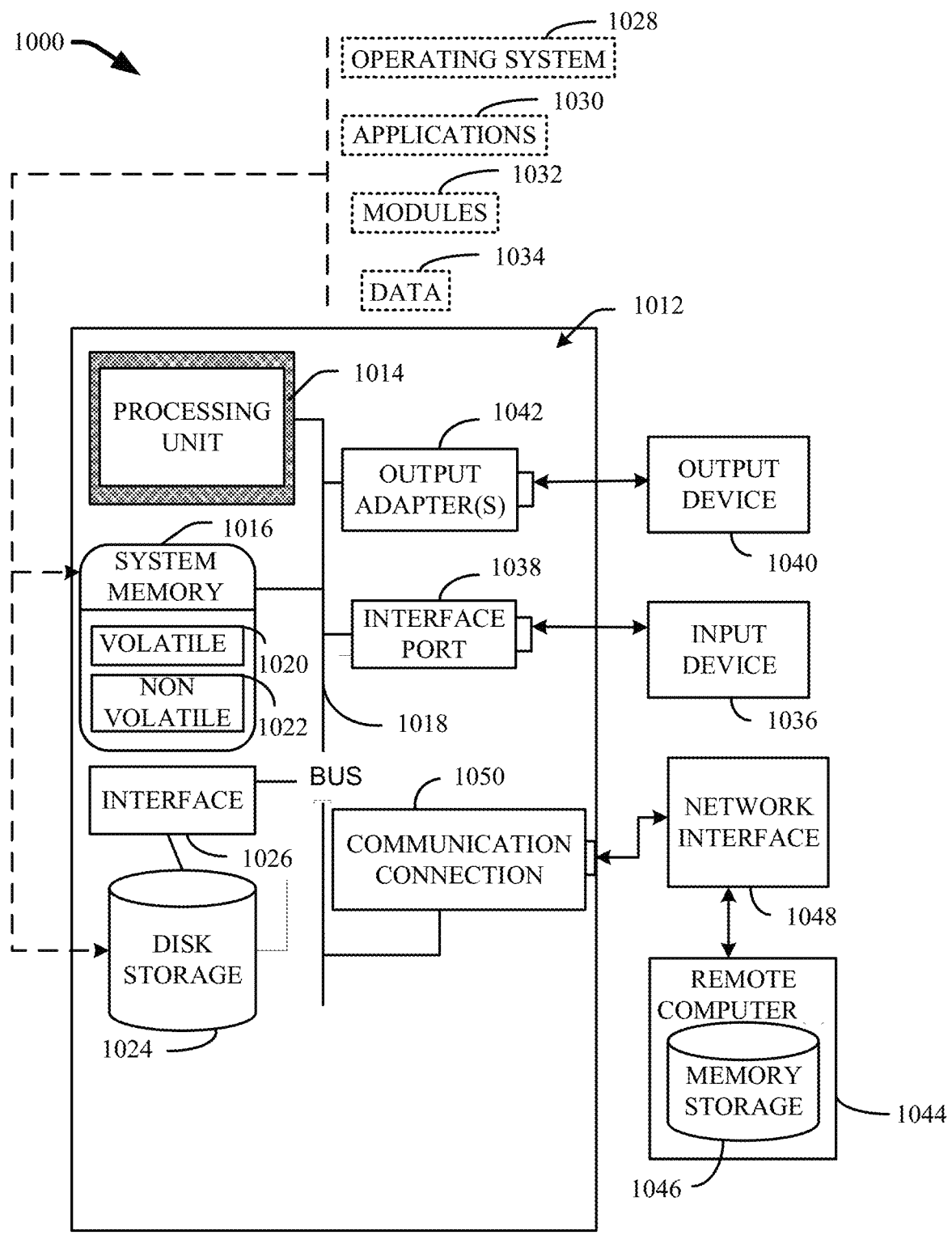
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can include a computer 1012. The computer 1012 can also include a processing unit 1014, a system memory 1016, and a system bus 1018. The system bus 1018 can operably couple system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structures including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire, and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, can be stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface can be used, such as interface 1026. FIG. 10 also depicts software that can act as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 can take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through one or more input devices 1036. Input devices 1036 can include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices can connect to the processing unit 1014 through the system bus 1018 via one or more interface ports 1038. The one or more Interface ports 1038 can include, for example, a serial port, a parallel port, a game port, and a universal serial bus (USB). One or more output devices 1040 can use some of the same type of ports as input device 1036. Thus, for example, a USB port can be used to provide input to computer 1012, and to output information from computer 1012 to an output device 1040. Output adapter 1042 can be provided to illustrate that there are some output devices 1040 like monitors, speakers, and printers, among other output devices 1040, which require special adapters. The output adapters 1042 can include, by way of illustration and not limitation, video and sound cards that provide a means of connection between the output device 1040 and the system bus 1018. It should be noted that other devices and/or systems of devices provide both input and output capabilities such as one or more remote computers 1044.

Computer 1012 can operate in a networked environment using logical connections to one or more remote computers, such as remote computer 1044. The remote computer 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer 1044. Remote computer 1044 can be logically connected to computer 1012 through a network interface 1048 and then physically connected via communication connection 1050. Further, operation can be distributed across multiple (local and remote) systems. Network interface 1048 can encompass wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). One or more communication connections 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

Embodiments of the present invention can be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of various aspects of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to customize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device including, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components including a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems, computer program products and computer-implemented methods. It is, of course, not possible to describe every conceivable combination of components, products and/or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
   a memory that stores computer executable components;
   a processor, operably coupled to the memory, and that executes the computer executable components stored in the memory, wherein the computer executable components comprise:
      a data analysis component that trains a neural network model to determine trust disposition values associated with human entity based on respective datasets associated with interactions with the human entities, wherein the interactions comprise artificial intelligence chatbot conversations;
      an evaluation component that determines, using the neural network model, a trust disposition value associated with a human entity by analyzing a dataset associated with interactions with the human entity, wherein the dataset comprises an artificial intelligence chatbot conversation with the human entity directed to at least one commitment involving the human entity with respect to at least one medical related experience of the human entity; and
      a prescription component that updates a status of a prescription associated with the human entity based on the trust disposition value.

2. The system of claim 1, wherein the data analysis component generates the dataset that comprises a plurality of features extracted from the interactions with the human entity.

3. The system of claim 2, wherein the plurality of features comprise features selected from a group consisting of a debtor, a creditor, an antecedent, and a consequent.

4. The system of claim 2, wherein the plurality of features delineates whether the commitment was fulfilled.

5. The system of claim 1, wherein at least some of the interactions are between the human entity and an artificial intelligence system.

6. The system of claim 1, wherein the prescription component updates the status of the prescription by performing an action selected from a group consisting of renewing the prescription, failing to renew the prescription, and modifying a dosage of a medicine.

7. The system of claim 1, wherein the prescription component updates the status of the prescription by comparing the trust disposition value to a predefined threshold.

8. A computer-implemented method, comprising:
    training, by a system operatively coupled to a processor, a machine learning model to determine trust disposition values associated with human entity based on respective datasets associated with interactions with the human entities, wherein the interactions comprise artificial intelligence chatbot conversations;
    determining, by the system, using the machine learning model, a trust disposition value associated with a human entity by analyzing a dataset associated with interactions with the human entity, wherein the dataset comprises an artificial intelligence a chatbot conversation with the human entity directed to at least one commitment involving the human entity with respect to at least one medical related experience of the human entity; and
    updating, by the system, a status of a prescription associated with the human entity based on the trust disposition value.

9. The computer-implemented method of claim 8, further comprising:
    generating, by the system, the dataset that comprises a plurality of features extracted from the interactions with the human entity.

10. The computer-implemented method of claim 9, wherein the plurality of features comprise features selected from a group consisting of a debtor, a creditor, an antecedent, and a consequent.

11. The computer-implemented method of claim 9, wherein the plurality of features delineates whether the commitment was fulfilled.

12. The computer-implemented method of claim 8, wherein at least some of the interactions are between the human entity and an artificial intelligence system.

13. The computer-implemented method of claim 8, further comprising:
    updating, by the system, the status of the prescription by performing an action selected from a group consisting of renewing the prescription, failing to renew the prescription, and modifying a dosage of a medicine.

14. The computer-implemented method of claim 8, further comprising:
    updating, by the system, the status of the prescription by comparing the trust disposition value to a predefined threshold.

15. A computer program product for autonomously updating a prescription, the computer program product comprising a computer readable storage medium having program instructions embodied therewith, the program instructions executable by a processor to cause the processor to:
    training a deep learning model to determine trust disposition values associated with human entity based on respective datasets associated with interactions with the human entities, wherein the interactions comprise artificial intelligence chatbot conversations;
    determine, using the deep learning model, a trust disposition value associated with a human entity by analyzing a dataset associated with interactions with the human entity, wherein the dataset comprises an artificial intelligence chatbot conversation with the human entity directed to at least one commitment involving the human entity with respect to at least one medical related experience of the human entity; and
    update a status of the prescription associated with the human entity based on the trust disposition value.

16. The computer program product of claim 15, wherein the program instructions further cause the processor to:
    generate the dataset that comprises a plurality of features extracted from the interactions with the human entity.

17. The computer program product of claim 16, wherein the plurality of features comprise features selected from a group consisting of a debtor, a creditor, an antecedent, and a consequent.

18. The computer program product of claim 16, wherein the plurality of features delineates whether the commitment was fulfilled.

19. The computer program product of claim 15, wherein at least some of the interactions are between the human entity and an artificial intelligence system.

20. The computer program product of claim 15, wherein the program instructions further cause the processor to:
    update the status of the prescription by performing an action selected from a group consisting of renew the prescription, fail to renew the prescription, and modify a dosage of a medicine.

* * * * *